(12) United States Patent
Rego, Jr.

(10) Patent No.: US 8,652,079 B2
(45) Date of Patent: Feb. 18, 2014

(54) COMPRESSION GARMENT HAVING AN EXTENSION

(75) Inventor: Richard P. Rego, Jr., Mansfield, MA (US)

(73) Assignee: Covidien LP, Mansfield, MA (US)

( * ) Notice: Subject to any disclaimer, the term of this patent is extended or adjusted under 35 U.S.C. 154(b) by 192 days.

(21) Appl. No.: 12/753,558

(22) Filed: Apr. 2, 2010

(65) Prior Publication Data

US 2011/0245742 A1 Oct. 6, 2011

(51) Int. Cl.
*A61H 9/00* (2006.01)
*A61F 5/00* (2006.01)
*A61F 5/37* (2006.01)

(52) U.S. Cl.
USPC ........... 601/151; 601/5; 601/148; 601/152; 128/878; 128/882; 602/13; 606/192

(58) Field of Classification Search
USPC ............ 601/5, 148, 151, 152; 128/878, 882; 602/13; 606/192
See application file for complete search history.

(56) References Cited

U.S. PATENT DOCUMENTS

| 908,959 A | 1/1909 | Cooke |
|---|---|---|
| 910,689 A | 1/1909 | Kelly et al. |
| 1,510,482 A | 10/1924 | Kramer |
| 1,608,239 A | 11/1926 | Rosett |
| 2,199,408 A | 5/1940 | La Liberte |
| 2,489,388 A | 11/1949 | Rubin |
| 2,533,504 A | 12/1950 | Poor |
| 2,638,915 A | 5/1953 | Mitchell |
| 2,676,587 A | 4/1954 | Corcoran |
| 2,694,395 A | 11/1954 | Brown |
| 2,880,721 A | 4/1959 | Corcoran |
| 2,896,612 A | 7/1959 | Bates et al. |
| 2,998,817 A | 9/1961 | Armstrong |
| 3,164,152 A | 1/1965 | Vere Nicoll |
| 3,245,405 A | 4/1966 | Gardner |
| 3,288,132 A | 11/1966 | Meredith |
| 3,351,055 A | 11/1967 | Gottfried |
| 3,454,010 A | 7/1969 | Lilligren et al. |
| 3,469,769 A | 9/1969 | Guenther |
| 3,473,527 A | 10/1969 | Spiro |

(Continued)

FOREIGN PATENT DOCUMENTS

| CA | 2582678 A1 | 4/2006 |
|---|---|---|
| DE | 19846922 A1 | 4/2000 |

(Continued)

OTHER PUBLICATIONS

Mittelman, Jonathan S., MD: "Effectiveness of Leg Compression in Preventing Venous Stasis", The American Journal of Surgery, Dec. 1982, p. 611-613, vol. 144, No. 6, Elsevier Publ., Bridgewater, NJ, USA.

(Continued)

*Primary Examiner* — Clinton T Ostrup
(74) *Attorney, Agent, or Firm* — John Paul Mello, Esq.

(57) ABSTRACT

A compression garment for applying compression therapy to a wearer's body including a compression sleeve having a proximal edge and a distal edge. The sleeve includes at least one bladder. A tube is attached to the bladder. A connector on the tube connects the tube to a source of compressed fluid for inflating the bladder. The distal edge of the compression sleeve has a first portion and a second portion jutting distally from the first portion.

10 Claims, 2 Drawing Sheets

(56) References Cited

U.S. PATENT DOCUMENTS

| | | |
|---|---|---|
| 3,504,675 A | 4/1970 | Bishop, Jr. |
| 3,561,435 A | 2/1971 | Nicholson |
| 3,568,227 A | 3/1971 | Dunham |
| 3,606,880 A | 9/1971 | Ogle, Jr. |
| 3,638,334 A | 2/1972 | Malikowski |
| 3,701,173 A | 10/1972 | Whitney |
| 3,728,875 A | 4/1973 | Hartigan et al. |
| 3,760,795 A | 9/1973 | Adelhed |
| 3,770,040 A | 11/1973 | De Cicco |
| 3,771,519 A | 11/1973 | Haake |
| 3,786,805 A | 1/1974 | Tourin |
| 3,824,992 A | 7/1974 | Nicholson et al. |
| 3,826,249 A | 7/1974 | Lee et al. |
| 3,862,629 A | 1/1975 | Rotta |
| 3,868,952 A | 3/1975 | Hatton |
| 3,877,426 A | 4/1975 | Nirschl |
| 3,878,839 A | 4/1975 | Norton et al. |
| 3,899,210 A | 8/1975 | Samhammer et al. |
| 3,901,221 A | 8/1975 | Nicholson et al. |
| 3,906,937 A | 9/1975 | Aronson |
| 3,920,006 A | 11/1975 | Lapidus |
| D239,981 S | 5/1976 | Arbuck et al. |
| 3,955,565 A | 5/1976 | Johnson, Jr. |
| 4,013,069 A | 3/1977 | Hasty |
| 4,029,087 A | 6/1977 | Dye et al. |
| 4,030,488 A | 6/1977 | Hasty |
| 4,054,129 A | 10/1977 | Byars et al. |
| 4,066,084 A | 1/1978 | Tillander |
| 4,076,022 A | 2/1978 | Walker |
| 4,091,804 A | 5/1978 | Hasty |
| 4,146,021 A | 3/1979 | Brosseau et al. |
| 4,149,529 A | 4/1979 | Copeland et al. |
| 4,149,541 A | 4/1979 | Gammons et al. |
| 4,153,050 A | 5/1979 | Bishop et al. |
| 4,156,425 A | 5/1979 | Arkans |
| 4,198,961 A | 4/1980 | Arkans |
| 4,201,203 A | 5/1980 | Applegate |
| 4,202,312 A | 5/1980 | Mori et al. |
| 4,202,325 A | 5/1980 | Villari et al. |
| 4,206,751 A | 6/1980 | Schneider |
| 4,207,875 A | 6/1980 | Arkans |
| 4,207,876 A * | 6/1980 | Annis ............................ 601/152 |
| 4,219,892 A | 9/1980 | Rigdon |
| 4,253,449 A | 3/1981 | Arkans et al. |
| 4,267,611 A | 5/1981 | Agulnick |
| 4,270,527 A | 6/1981 | Peters et al. |
| 4,280,485 A | 7/1981 | Arkans |
| 4,294,240 A | 10/1981 | Thill |
| 4,300,245 A | 11/1981 | Saunders |
| 4,308,862 A | 1/1982 | Kalmar |
| 4,311,135 A | 1/1982 | Brueckner et al. |
| 4,320,746 A | 3/1982 | Arkans et al. |
| 4,352,253 A | 10/1982 | Oswalt |
| 4,355,632 A | 10/1982 | Sandman |
| 4,363,125 A | 12/1982 | Brewer et al. |
| 4,372,297 A | 2/1983 | Perlin |
| 4,375,217 A | 3/1983 | Arkans |
| 4,379,217 A | 4/1983 | Youmans |
| 4,402,312 A * | 9/1983 | Villari et al. ................ 601/152 |
| 4,408,599 A | 10/1983 | Mummert |
| 4,417,587 A | 11/1983 | Ichinomiya et al. |
| 4,437,269 A | 3/1984 | Shaw |
| 4,442,834 A | 4/1984 | Tucker et al. |
| 4,445,505 A | 5/1984 | Labour et al. |
| 4,453,538 A | 6/1984 | Whitney |
| 4,522,197 A | 6/1985 | Hasegawa |
| 4,531,516 A | 7/1985 | Poole et al. |
| 4,547,906 A | 10/1985 | Nishida et al. |
| 4,547,919 A | 10/1985 | Wang |
| 4,552,821 A | 11/1985 | Gibbard et al. |
| 4,580,816 A | 4/1986 | Campbell et al. |
| 4,593,692 A | 6/1986 | Flowers |
| 4,597,384 A | 7/1986 | Whitney |
| 4,614,180 A | 9/1986 | Gardner et al. |
| 4,624,244 A | 11/1986 | Taheri |
| 4,650,452 A | 3/1987 | Jensen |
| 4,657,003 A | 4/1987 | Wirtz |
| 4,682,588 A | 7/1987 | Curlee |
| 4,696,289 A | 9/1987 | Gardner et al. |
| 4,699,424 A | 10/1987 | Andres et al. |
| 4,702,232 A | 10/1987 | Gardner et al. |
| 4,703,750 A | 11/1987 | Sebastian et al. |
| 4,706,658 A | 11/1987 | Cronin |
| 4,722,332 A | 2/1988 | Saggers |
| 4,730,606 A | 3/1988 | Leininger |
| 4,762,121 A | 8/1988 | Shienfeld |
| 4,773,397 A | 9/1988 | Wright et al. |
| 4,805,620 A | 2/1989 | Meistrell |
| 4,809,684 A | 3/1989 | Gardner et al. |
| 4,827,912 A | 5/1989 | Carrington et al. |
| 4,832,010 A | 5/1989 | Lerman |
| RE32,939 E | 6/1989 | Gardner et al. |
| RE32,940 E | 6/1989 | Gardner et al. |
| 4,836,194 A | 6/1989 | Sebastian et al. |
| 4,836,691 A | 6/1989 | Suzuki et al. |
| D302,301 S | 7/1989 | Robinette-Lehman |
| 4,846,189 A | 7/1989 | Sun |
| 4,869,265 A | 9/1989 | McEwen |
| 4,872,448 A | 10/1989 | Johnson, Jr. |
| 4,876,788 A | 10/1989 | Steer et al. |
| 4,883,073 A | 11/1989 | Aziz |
| 4,886,053 A | 12/1989 | Neal |
| 4,898,160 A | 2/1990 | Brownlee |
| 4,913,136 A | 4/1990 | Chong et al. |
| 4,938,207 A | 7/1990 | Vargo |
| 4,938,208 A * | 7/1990 | Dye ................................ 602/13 |
| 4,938,226 A | 7/1990 | Danielsson et al. |
| 4,945,571 A | 8/1990 | Calvert |
| 4,947,834 A | 8/1990 | Kartheus et al. |
| 4,957,105 A | 9/1990 | Kurth |
| 4,960,115 A | 10/1990 | Ranciato |
| 4,964,402 A | 10/1990 | Grim et al. |
| 4,979,953 A | 12/1990 | Spence |
| 4,989,273 A | 2/1991 | Cromartie |
| 4,997,452 A | 3/1991 | Kovach et al. |
| 5,007,411 A | 4/1991 | Dye |
| 5,014,681 A | 5/1991 | Neeman et al. |
| 5,022,387 A | 6/1991 | Hasty |
| 5,031,604 A | 7/1991 | Dye |
| 5,048,536 A | 9/1991 | McEwen |
| 5,052,377 A | 10/1991 | Frajdenrajch |
| 5,062,414 A | 11/1991 | Grim |
| 5,069,219 A | 12/1991 | Knoblich |
| 5,071,415 A | 12/1991 | Takemoto |
| 5,080,951 A | 1/1992 | Guthrie |
| 5,082,284 A | 1/1992 | Reed |
| 5,109,832 A | 5/1992 | Proctor et al. |
| 5,117,812 A | 6/1992 | McWhorter |
| 5,120,300 A | 6/1992 | Shaw |
| 5,135,473 A | 8/1992 | Epler et al. |
| 5,139,476 A | 8/1992 | Peters |
| 5,139,477 A | 8/1992 | Peters |
| 5,139,479 A | 8/1992 | Peters |
| 5,146,932 A | 9/1992 | McCabe |
| 5,156,629 A | 10/1992 | Shane et al. |
| 5,158,541 A | 10/1992 | McCurley |
| 5,168,576 A | 12/1992 | Krent et al. |
| 5,172,689 A | 12/1992 | Wright |
| D332,495 S | 1/1993 | Lake |
| 5,179,941 A | 1/1993 | Siemssen et al. |
| 5,181,522 A | 1/1993 | McEwen |
| 5,186,163 A | 2/1993 | Dye |
| 5,193,549 A | 3/1993 | Bellin et al. |
| 5,211,162 A | 5/1993 | Gillen, Jr. et al. |
| 5,226,245 A | 7/1993 | Lamont |
| 5,230,335 A | 7/1993 | Johnson, Jr. et al. |
| 5,245,990 A | 9/1993 | Bertinin |
| 5,259,397 A | 11/1993 | McCabe |
| 5,261,871 A | 11/1993 | Greenfield |
| 5,263,473 A | 11/1993 | McWhorter |
| 5,277,695 A | 1/1994 | Johnson, Jr. et al. |
| 5,277,697 A | 1/1994 | France et al. |
| 5,288,286 A | 2/1994 | Davis |
| 5,312,431 A | 5/1994 | McEwen |

(56) References Cited

U.S. PATENT DOCUMENTS

| | | |
|---|---|---|
| 5,314,455 A | 5/1994 | Johnson, Jr. et al. |
| 5,334,135 A | 8/1994 | Grim et al. |
| 5,342,285 A | 8/1994 | Dye |
| 5,354,260 A | 10/1994 | Cook |
| 5,378,224 A | 1/1995 | Billotti |
| 5,383,894 A | 1/1995 | Dye |
| 5,383,919 A | 1/1995 | Kelly et al. |
| 5,385,538 A | 1/1995 | Mann |
| 5,389,065 A | 2/1995 | Johnson, Jr. |
| 5,391,141 A | 2/1995 | Hamilton |
| 5,399,153 A | 3/1995 | Caprio, Jr. et al. |
| 5,403,265 A | 4/1995 | Berguer et al. |
| 5,406,661 A | 4/1995 | Pekar |
| 5,407,421 A | 4/1995 | Goldsmith |
| D358,216 S | 5/1995 | Dye |
| 5,413,582 A | 5/1995 | Eaton |
| 5,419,757 A | 5/1995 | Daneshvar |
| 5,425,701 A | 6/1995 | Oster et al. |
| 5,435,009 A | 7/1995 | Schild et al. |
| 5,437,595 A | 8/1995 | Smith |
| 5,437,610 A | 8/1995 | Cariapa et al. |
| 5,441,533 A | 8/1995 | Johnson et al. |
| 5,443,440 A | 8/1995 | Tumey et al. |
| 5,449,341 A | 9/1995 | Harris |
| 5,449,379 A | 9/1995 | Hadtke |
| 5,450,858 A | 9/1995 | Zablotsky et al. |
| 5,451,201 A | 9/1995 | Prengler |
| 5,453,081 A | 9/1995 | Hansen |
| 5,458,265 A | 10/1995 | Hester et al. |
| 5,462,517 A | 10/1995 | Mann |
| 5,466,250 A | 11/1995 | Johnson, Jr. et al. |
| 5,470,156 A | 11/1995 | May |
| 5,478,119 A | 12/1995 | Dye |
| 5,489,259 A | 2/1996 | Jacobs et al. |
| 5,496,262 A | 3/1996 | Johnson, Jr. et al. |
| 5,503,620 A | 4/1996 | Danzger |
| 5,511,552 A | 4/1996 | Johnson |
| 5,513,658 A | 5/1996 | Goseki |
| 5,514,081 A | 5/1996 | Mann |
| 5,514,155 A | 5/1996 | Daneshvar |
| 5,554,105 A | 9/1996 | Taylor |
| D376,013 S | 11/1996 | Sandman et al. |
| 5,575,762 A | 11/1996 | Peeler et al. |
| 5,578,055 A | 11/1996 | McEwen |
| 5,584,798 A | 12/1996 | Fox |
| 5,588,954 A | 12/1996 | Ribando et al. |
| 5,588,955 A | 12/1996 | Johnson, Jr. et al. |
| 5,588,956 A | 12/1996 | Billotti |
| 5,591,200 A | 1/1997 | Cone et al. |
| 5,591,337 A | 1/1997 | Lynn et al. |
| 5,603,690 A | 2/1997 | Barry |
| 5,609,570 A | 3/1997 | Lamont |
| 5,620,411 A | 4/1997 | Schumann et al. |
| 5,626,556 A | 5/1997 | Tobler et al. |
| 5,626,557 A | 5/1997 | Mann |
| 5,634,889 A | 6/1997 | Gardner et al. |
| 5,637,106 A | 6/1997 | Mitchell et al. |
| 5,640,714 A | 6/1997 | Tanaka |
| 5,649,954 A | 7/1997 | McEwen |
| 5,653,244 A | 8/1997 | Shaw |
| D383,547 S | 9/1997 | Mason et al. |
| 5,664,270 A | 9/1997 | Bell et al. |
| 5,669,872 A | 9/1997 | Fox |
| 5,674,262 A | 10/1997 | Tumey |
| 5,695,453 A | 12/1997 | Neal |
| 5,704,999 A | 1/1998 | Lukich et al. |
| 5,711,757 A | 1/1998 | Bryant |
| 5,717,996 A | 2/1998 | Feldmann |
| 5,728,055 A | 3/1998 | Sebastian |
| 5,728,057 A | 3/1998 | Ouellette et al. |
| 5,730,710 A | 3/1998 | Eichhorn et al. |
| 5,733,304 A | 3/1998 | Spence |
| 5,741,295 A | 4/1998 | McEwen |
| 5,746,213 A | 5/1998 | Marks |
| 5,765,298 A | 6/1998 | Potter et al. |
| 5,769,800 A | 6/1998 | Gelfand et al. |
| 5,769,801 A | 6/1998 | Tumey et al. |
| 5,790,998 A | 8/1998 | Crescimbeni |
| 5,795,312 A | 8/1998 | Dye |
| 5,797,851 A | 8/1998 | Byrd |
| 5,823,981 A | 10/1998 | Grim et al. |
| 5,833,639 A | 11/1998 | Nunes et al. |
| 5,840,049 A | 11/1998 | Tumey et al. |
| 5,843,007 A | 12/1998 | McEwen et al. |
| D403,775 S | 1/1999 | Davis et al. |
| D405,884 S | 2/1999 | Roper |
| 5,876,359 A | 3/1999 | Bock et al. |
| 5,891,065 A | 4/1999 | Cariapa et al. |
| 5,894,682 A | 4/1999 | Broz |
| D411,301 S | 6/1999 | Hampson et al. |
| 5,916,183 A | 6/1999 | Reid |
| 5,925,010 A | 7/1999 | Caprio, Jr. |
| 5,926,850 A | 7/1999 | Han |
| 5,938,628 A | 8/1999 | Oguri et al. |
| 5,951,502 A | 9/1999 | Peeler et al. |
| 5,957,872 A | 9/1999 | Flick |
| 5,966,763 A | 10/1999 | Thomas et al. |
| 5,968,072 A | 10/1999 | Hite et al. |
| 5,970,519 A | 10/1999 | Weber |
| 5,976,099 A | 11/1999 | Kellogg |
| 5,976,300 A | 11/1999 | Buchanan et al. |
| 5,988,704 A | 11/1999 | Ryhman |
| 5,989,204 A | 11/1999 | Lina |
| 5,991,654 A | 11/1999 | Tumey et al. |
| 5,997,495 A | 12/1999 | Cook et al. |
| 5,997,981 A | 12/1999 | McCormack et al. |
| 6,001,119 A | 12/1999 | Hampson et al. |
| 6,007,559 A | 12/1999 | Arkans |
| 6,010,471 A | 1/2000 | Ben-Noon |
| 6,021,780 A | 2/2000 | Darby |
| 6,036,718 A | 3/2000 | Ledford et al. |
| 6,048,326 A | 4/2000 | Davis et al. |
| 6,051,016 A | 4/2000 | Mesaros et al. |
| 6,056,713 A | 5/2000 | Hayashi |
| 6,062,244 A | 5/2000 | Arkans |
| 6,066,217 A | 5/2000 | Dibble et al. |
| 6,076,193 A | 6/2000 | Hood |
| 6,080,120 A | 6/2000 | Sandman et al. |
| D428,153 S | 7/2000 | Davis |
| 6,110,135 A | 8/2000 | Madow et al. |
| 6,120,469 A | 9/2000 | Bruder |
| 6,126,683 A | 10/2000 | Momtaheni |
| 6,129,688 A | 10/2000 | Arkans |
| 6,129,695 A | 10/2000 | Peters et al. |
| 6,135,116 A | 10/2000 | Vogel et al. |
| 6,145,143 A | 11/2000 | Hicks et al. |
| 6,149,600 A | 11/2000 | Poorman-Ketchum |
| 6,149,616 A | 11/2000 | Szlema et al. |
| 6,152,495 A | 11/2000 | Hoffmann et al. |
| 6,152,893 A | 11/2000 | Pigg et al. |
| 6,168,539 B1 | 1/2001 | Maina |
| 6,171,271 B1 | 1/2001 | Hörnberg |
| 6,179,796 B1 | 1/2001 | Waldridge |
| 6,197,045 B1 | 3/2001 | Carson |
| 6,203,510 B1 | 3/2001 | Takeuchi et al. |
| 6,209,159 B1 | 4/2001 | Murphy |
| 6,212,719 B1 | 4/2001 | Thomas et al. |
| 6,231,507 B1 | 5/2001 | Zikorus et al. |
| 6,231,532 B1 | 5/2001 | Watson et al. |
| 6,245,023 B1 | 6/2001 | Clemmons |
| 6,254,554 B1 | 7/2001 | Turtzo |
| 6,257,626 B1 | 7/2001 | Campau |
| 6,257,627 B1 | 7/2001 | Fujiwara et al. |
| 6,260,201 B1 | 7/2001 | Rankin |
| 6,290,662 B1 | 9/2001 | Morris et al. |
| 6,290,664 B1 | 9/2001 | Nauert |
| 6,315,745 B1 | 11/2001 | Kloecker |
| 6,319,215 B1 | 11/2001 | Manor et al. |
| 6,322,530 B1 | 11/2001 | Johnson, Jr. et al. |
| 6,336,935 B1 | 1/2002 | Davis et al. |
| 6,338,723 B1 | 1/2002 | Carpenter et al. |
| 6,349,506 B1 | 2/2002 | Pace et al. |
| 6,358,219 B1 | 3/2002 | Arkans |
| 6,368,357 B1 | 4/2002 | Schon et al. |

(56) References Cited

U.S. PATENT DOCUMENTS

| | | |
|---|---|---|
| 6,375,633 B1 | 4/2002 | Endress et al. |
| 6,385,778 B1 | 5/2002 | Johnson |
| 6,385,864 B1 | 5/2002 | Sell, Jr. et al. |
| 6,387,065 B1 | 5/2002 | Tumey |
| 6,402,879 B1 | 6/2002 | Tawney et al. |
| 6,409,691 B1 | 6/2002 | Dakin et al. |
| 6,423,053 B1 | 7/2002 | Lee |
| 6,436,064 B1 | 8/2002 | Kloecker |
| 6,440,093 B1 | 8/2002 | McEwen et al. |
| 6,447,460 B1 | 9/2002 | Zheng et al. |
| 6,463,934 B1 | 10/2002 | Johnson, Jr. et al. |
| 6,468,237 B1 | 10/2002 | Lina |
| 6,478,757 B1 | 11/2002 | Barak |
| 6,478,761 B2 | 11/2002 | Bracamonte-Sommer |
| 6,488,643 B1 | 12/2002 | Tumey et al. |
| 6,494,852 B1 | 12/2002 | Barak et al. |
| 6,508,205 B1 | 1/2003 | Zink |
| 6,520,926 B2 | 2/2003 | Hall |
| 6,526,597 B1 | 3/2003 | Shepard |
| 6,527,727 B2 | 3/2003 | Itonaga et al. |
| 6,537,298 B2 | 3/2003 | Dedo |
| 6,540,707 B1 | 4/2003 | Stark et al. |
| 6,544,202 B2 | 4/2003 | McEwen et al. |
| 6,549,748 B2 | 4/2003 | Miura |
| 6,551,280 B1 | 4/2003 | Knighton et al. |
| 6,554,785 B1 | 4/2003 | Sroufe et al. |
| 6,557,704 B1 | 5/2003 | Randolph |
| 6,558,338 B1 | 5/2003 | Wasserman |
| 6,562,060 B1 | 5/2003 | Momtaheni |
| 6,589,267 B1 | 7/2003 | Hui |
| 6,589,534 B1 | 7/2003 | Shaul et al. |
| 6,592,534 B1 | 7/2003 | Rutt et al. |
| 6,593,508 B1 | 7/2003 | Harder |
| 6,598,249 B2 | 7/2003 | Pajanacci et al. |
| D478,995 S | 8/2003 | Cipra et al. |
| 6,616,622 B1 | 9/2003 | Barberio |
| 6,618,859 B1 | 9/2003 | Kadymir et al. |
| 6,629,941 B1 | 10/2003 | Ishibashi et al. |
| 6,645,165 B2 | 11/2003 | Waldridge et al. |
| D484,986 S | 1/2004 | Cipra et al. |
| 6,676,614 B1 | 1/2004 | Hansen et al. |
| 6,682,547 B2 | 1/2004 | McEwen et al. |
| 6,685,661 B2 | 2/2004 | Peled |
| 6,719,711 B1 | 4/2004 | Islava |
| 6,726,641 B2 | 4/2004 | Chiang et al. |
| 6,746,470 B2 | 6/2004 | McEwen et al. |
| 6,762,337 B2 | 7/2004 | Boukanov et al. |
| 6,762,338 B2 | 7/2004 | Harder |
| 6,842,915 B2 | 1/2005 | Turner et al. |
| 6,846,294 B2 | 1/2005 | Rastegar et al. |
| 6,846,295 B1 | 1/2005 | Ben-Nun |
| 6,849,057 B2 | 2/2005 | Satou et al. |
| 6,852,089 B2 | 2/2005 | Kloecker et al. |
| 6,860,862 B2 | 3/2005 | Waldridge et al. |
| 6,862,989 B2 | 3/2005 | Belanger et al. |
| 6,866,636 B2 | 3/2005 | Inoue et al. |
| 6,869,409 B2 | 3/2005 | Rothman et al. |
| D506,553 S | 6/2005 | Tesluk |
| 6,945,944 B2 | 9/2005 | Kuiper et al. |
| D510,626 S | 10/2005 | Krahner et al. |
| 6,973,690 B2 | 12/2005 | Muci et al. |
| 6,984,215 B2 | 1/2006 | Shah et al. |
| 6,991,613 B2 | 1/2006 | Sensabaugh |
| 7,011,640 B2 | 3/2006 | Patterson et al. |
| 7,022,096 B1 | 4/2006 | Alfieri |
| 7,041,074 B1 | 5/2006 | Averianov et al. |
| 7,044,924 B1 | 5/2006 | Roth et al. |
| 7,048,703 B2 | 5/2006 | Riach |
| D533,668 S | 12/2006 | Brown |
| 7,166,077 B2 | 1/2007 | Millay et al. |
| 7,217,249 B2 | 5/2007 | Scott |
| D545,972 S | 7/2007 | Wierenga et al. |
| 7,237,272 B2 | 7/2007 | Botcher |
| 7,238,080 B2 | 7/2007 | Gimble |
| 7,258,676 B2 | 8/2007 | Calderon et al. |
| D550,367 S | 9/2007 | Nash |
| 7,276,037 B2 | 10/2007 | Ravikumar |
| 7,276,039 B2 | 10/2007 | Garelick et al. |
| 7,278,980 B1 | 10/2007 | Garelick et al. |
| 7,282,038 B2 | 10/2007 | Gillis et al. |
| 7,285,103 B2 | 10/2007 | Nathanson |
| 7,288,076 B2 | 10/2007 | Grim et al. |
| 7,297,128 B2 | 11/2007 | Binder et al. |
| 7,300,410 B1 | 11/2007 | Weber |
| 7,303,539 B2 | 12/2007 | Binder et al. |
| 7,306,568 B2 | 12/2007 | Diana |
| 7,310,847 B2 | 12/2007 | Bolkan et al. |
| 7,318,812 B2 | 1/2008 | Taylor et al. |
| D562,461 S | 2/2008 | Nash |
| D562,462 S | 2/2008 | Muir et al. |
| 7,326,227 B2 | 2/2008 | Dedo et al. |
| 7,329,232 B2 | 2/2008 | Lipshaw et al. |
| 7,351,217 B2 | 4/2008 | Scherpenborg |
| 7,353,770 B2 | 4/2008 | Sanguinetti |
| 7,354,410 B2 | 4/2008 | Perry et al. |
| 7,354,411 B2 | 4/2008 | Perry et al. |
| 7,374,550 B2 | 5/2008 | Hansen et al. |
| D577,124 S | 9/2008 | Freeland et al. |
| 7,424,936 B2 | 9/2008 | McClellan |
| 7,442,175 B2 | 10/2008 | Meyer et al. |
| 7,465,283 B2 | 12/2008 | Grim et al. |
| 7,468,048 B2 | 12/2008 | Meehan |
| 7,473,816 B2 | 1/2009 | Hall |
| D594,561 S | 6/2009 | Freeland et al. |
| 7,543,399 B2 | 6/2009 | Kilgore et al. |
| 7,559,908 B2 | 7/2009 | Ravikumar |
| 7,578,799 B2 | 8/2009 | Thorsteinsson et al. |
| 7,591,796 B1 | 9/2009 | Barak et al. |
| 7,591,797 B2 | 9/2009 | Hakonson et al. |
| 7,597,675 B2 | 10/2009 | Ingimundarson et al. |
| 7,615,027 B2 | 11/2009 | Nordt, III et al. |
| 7,618,389 B2 | 11/2009 | Nordt, III et al. |
| 7,625,348 B2 | 12/2009 | Young et al. |
| 7,637,879 B2 | 12/2009 | Barak et al. |
| D608,006 S | 1/2010 | Avitable et al. |
| 7,654,117 B2 | 2/2010 | Barnett |
| 7,748,090 B2 | 7/2010 | Seth et al. |
| 7,766,890 B2 | 8/2010 | Ito et al. |
| 7,827,624 B1 | 11/2010 | Cole |
| 8,177,734 B2 | 5/2012 | Vess |
| 2001/0018564 A1 | 8/2001 | Manor et al. |
| 2002/0068886 A1 | 6/2002 | Lin |
| 2002/0069731 A1 | 6/2002 | Soucy |
| 2002/0115949 A1 | 8/2002 | Kuslich et al. |
| 2003/0018313 A1 | 1/2003 | Tanzer et al. |
| 2003/0083605 A1 | 5/2003 | Edmund |
| 2003/0191420 A1* | 10/2003 | Kuiper et al. ............... 601/152 |
| 2003/0199922 A1 | 10/2003 | Buckman |
| 2004/0010212 A1 | 1/2004 | Kuiper et al. |
| 2004/0039317 A1 | 2/2004 | Souney et al. |
| 2004/0039413 A1 | 2/2004 | Akerfeldt et al. |
| 2004/0054306 A1 | 3/2004 | Roth et al. |
| 2004/0068290 A1 | 4/2004 | Bates et al. |
| 2004/0097860 A1 | 5/2004 | Tauber |
| 2004/0158283 A1 | 8/2004 | Shook et al. |
| 2004/0158285 A1 | 8/2004 | Pillai |
| 2004/0176715 A1 | 9/2004 | Nelson |
| 2004/0181156 A1 | 9/2004 | Kingsford et al. |
| 2004/0181254 A1 | 9/2004 | Choi et al. |
| 2004/0199090 A1 | 10/2004 | Sanders et al. |
| 2004/0210167 A1 | 10/2004 | Webster |
| 2004/0236258 A1 | 11/2004 | Burns et al. |
| 2005/0070828 A1 | 3/2005 | Hampson et al. |
| 2005/0154336 A1 | 7/2005 | Kloecker et al. |
| 2005/0187503 A1 | 8/2005 | Tordella et al. |
| 2005/0209545 A1 | 9/2005 | Farrow et al. |
| 2005/0242315 A1 | 11/2005 | Lund |
| 2006/0010574 A1 | 1/2006 | Linnane et al. |
| 2006/0020236 A1 | 1/2006 | Ben-Nun |
| 2006/0135894 A1 | 6/2006 | Linnane et al. |
| 2006/0137072 A1 | 6/2006 | Visco et al. |
| 2006/0142719 A1 | 6/2006 | Vogt et al. |
| 2006/0189907 A1 | 8/2006 | Pick et al. |
| 2006/0211965 A1 | 9/2006 | Horn et al. |

(56) References Cited

U.S. PATENT DOCUMENTS

| | | |
|---|---|---|
| 2007/0038167 A1 | 2/2007 | Tabron et al. |
| 2007/0088239 A1 | 4/2007 | Roth et al. |
| 2007/0129658 A1 | 6/2007 | Hampson et al. |
| 2007/0135743 A1 | 6/2007 | Meyer |
| 2007/0135835 A1 | 6/2007 | McEwen et al. |
| 2007/0135836 A1 | 6/2007 | McEwen et al. |
| 2007/0161933 A1 | 7/2007 | Ravikumar |
| 2007/0167892 A1 | 7/2007 | Gramza et al. |
| 2007/0167895 A1 | 7/2007 | Gramza et al. |
| 2007/0179416 A1 | 8/2007 | Obrien et al. |
| 2007/0197944 A1 | 8/2007 | Bruce et al. |
| 2007/0219580 A1 | 9/2007 | McEwen et al. |
| 2007/0244506 A1 | 10/2007 | McEwen et al. |
| 2007/0260162 A1 | 11/2007 | Meyer et al. |
| 2007/0261789 A1 | 11/2007 | Giori |
| 2007/0276310 A1 | 11/2007 | Lipshaw et al. |
| 2007/0276311 A1 | 11/2007 | Wieringa et al. |
| 2007/0282233 A1 | 12/2007 | Meyer et al. |
| 2008/0000477 A1 | 1/2008 | Huster et al. |
| 2008/0004555 A1 | 1/2008 | Reis et al. |
| 2008/0004560 A1 | 1/2008 | Miskie |
| 2008/0021363 A1 | 1/2008 | Fee |
| 2008/0023423 A1 | 1/2008 | Duffy |
| 2008/0064996 A1 | 3/2008 | Bretl et al. |
| 2008/0071202 A1 | 3/2008 | Nardi et al. |
| 2008/0072629 A1 | 3/2008 | Gehring |
| 2008/0086071 A1 | 4/2008 | Weatherly |
| 2008/0103397 A1 | 5/2008 | Barak |
| 2008/0119771 A1 | 5/2008 | Jaccard |
| 2008/0141428 A1 | 6/2008 | Kapah et al. |
| 2008/0143007 A1 | 6/2008 | Tuma |
| 2008/0183115 A1 | 7/2008 | Pierce |
| 2008/0188786 A1 | 8/2008 | Hickling |
| 2008/0208092 A1 | 8/2008 | Sawa |
| 2008/0234615 A1 | 9/2008 | Cook et al. |
| 2008/0243173 A1 | 10/2008 | Thorpe |
| 2008/0245361 A1 | 10/2008 | Brown |
| 2008/0249440 A1 | 10/2008 | Avitable et al. |
| 2008/0249441 A1 | 10/2008 | Avitable et al. |
| 2008/0249442 A1 | 10/2008 | Brown et al. |
| 2008/0249443 A1 | 10/2008 | Avitable et al. |
| 2008/0249444 A1 | 10/2008 | Avitable et al. |
| 2008/0249447 A1* | 10/2008 | Brown et al. .................. 602/13 |
| 2008/0249449 A1 | 10/2008 | Brown et al. |
| 2008/0249455 A1 | 10/2008 | Brown et al. |
| 2008/0249559 A1 | 10/2008 | Brown et al. |
| 2008/0250551 A1 | 10/2008 | Mazzarolo |
| 2008/0255485 A1 | 10/2008 | Johnson et al. |
| 2008/0281351 A1 | 11/2008 | Croushorn et al. |
| 2008/0306420 A1 | 12/2008 | Vess |
| 2008/0312682 A1 | 12/2008 | Shams et al. |
| 2009/0005718 A1 | 1/2009 | Lightbourne |
| 2009/0062703 A1 | 3/2009 | Meyer et al. |
| 2009/0064919 A1 | 3/2009 | Greenwald |
| 2009/0076432 A1 | 3/2009 | Winkler |
| 2009/0082708 A1 | 3/2009 | Scott et al. |
| 2009/0099562 A1 | 4/2009 | Ingimudarson et al. |
| 2009/0110890 A1 | 4/2009 | Garza et al. |
| 2009/0124944 A1 | 5/2009 | Ravikumar |
| 2009/0133446 A1 | 5/2009 | Burrow et al. |
| 2009/0137938 A1 | 5/2009 | Parivash |
| 2009/0163842 A1 | 6/2009 | Cropper |
| 2009/0171223 A1 | 7/2009 | McEwen et al. |
| 2009/0177222 A1 | 7/2009 | Brown et al. |
| 2009/0198160 A1 | 8/2009 | Coyne |
| 2009/0198261 A1 | 8/2009 | Schweikert |
| 2009/0227917 A1 | 9/2009 | Nardi |
| 2009/0227919 A1 | 9/2009 | Nardi et al. |
| 2009/0227922 A1 | 9/2009 | Nardi et al. |
| 2009/0234265 A1 | 9/2009 | Reid et al. |
| 2009/0270910 A1 | 10/2009 | Hargens et al. |
| 2009/0278707 A1 | 11/2009 | Biggins et al. |
| 2009/0281470 A1 | 11/2009 | Sandusky et al. |
| 2009/0299249 A1 | 12/2009 | Wilkes et al. |
| 2009/0312681 A1 | 12/2009 | McSpadden et al. |
| 2009/0320174 A1 | 12/2009 | Turner |
| 2009/0326576 A1 | 12/2009 | Ben-Nun |
| 2010/0004575 A1 | 1/2010 | Vess |
| 2010/0004676 A1 | 1/2010 | McEwen et al. |
| 2010/0010408 A1 | 1/2010 | Linares |
| 2010/0016771 A1 | 1/2010 | Arbesman et al. |
| 2010/0022930 A1 | 1/2010 | Koby et al. |
| 2010/0037369 A1 | 2/2010 | Reichert |
| 2010/0042026 A1 | 2/2010 | Kloecker et al. |
| 2010/0042028 A1 | 2/2010 | Frank et al. |
| 2010/0081975 A1 | 4/2010 | Avitable et al. |
| 2010/0081977 A1 | 4/2010 | Vess |
| 2010/0210982 A1 | 8/2010 | Balachandran et al. |
| 2012/0078146 A1 | 3/2012 | Deshpande |

FOREIGN PATENT DOCUMENTS

| | | |
|---|---|---|
| EP | 0303029 A1 | 2/1989 |
| EP | 0408049 A2 | 1/1991 |
| EP | 0861651 A1 | 9/1998 |
| EP | 1468816 A1 | 10/2004 |
| FR | 2813770 A1 | 3/2002 |
| GB | 2061086 A | 5/1981 |
| GB | 2178663 A | 2/1987 |
| GB | 2183483 A | 6/1987 |
| GB | 2313784 A | 12/1997 |
| GB | 2373444 A | 9/2002 |
| JP | 59218154 A | 12/1984 |
| JP | 60135110 U | 9/1985 |
| JP | 2002065782 | 3/2002 |
| JP | 2003310312 A | 11/2003 |
| JP | 2004081709 | 3/2004 |
| JP | 2005066247 | 3/2005 |
| JP | 2009000277 A | 1/2009 |
| WO | 96/20685 A1 | 7/1996 |
| WO | 2005082315 A1 | 9/2005 |
| WO | 2006083865 A2 | 8/2006 |

OTHER PUBLICATIONS

Tyco Healthcare Kendall, SCD Response Catalog, Mar. 2000, pp. 1-2.
Tyco Healthcare Kendall, SCD Soft Sleeve Catalog, Apr. 2001, pp. 1-2.
The Kendall Company, Vascular Therapy Products Catalog, Jan. 1996, pp. 8-5 thru 8-7.
The Kendall Company, The New SCD Compression Sleeve, Aug. 1993, pp. 1-2.
Tyco Healthcare Kendall, Prevention Gets Personal Mar. 2001, pp. 1, 2, 4.
Kendall SCD, Sequential Compression Sleeves, Patent Information, Jan. 1993, 6 pages.
Extended European Search Report issued Jun. 13, 2013 in related European Patent Application No. 11002241.5, 6 pages.

* cited by examiner

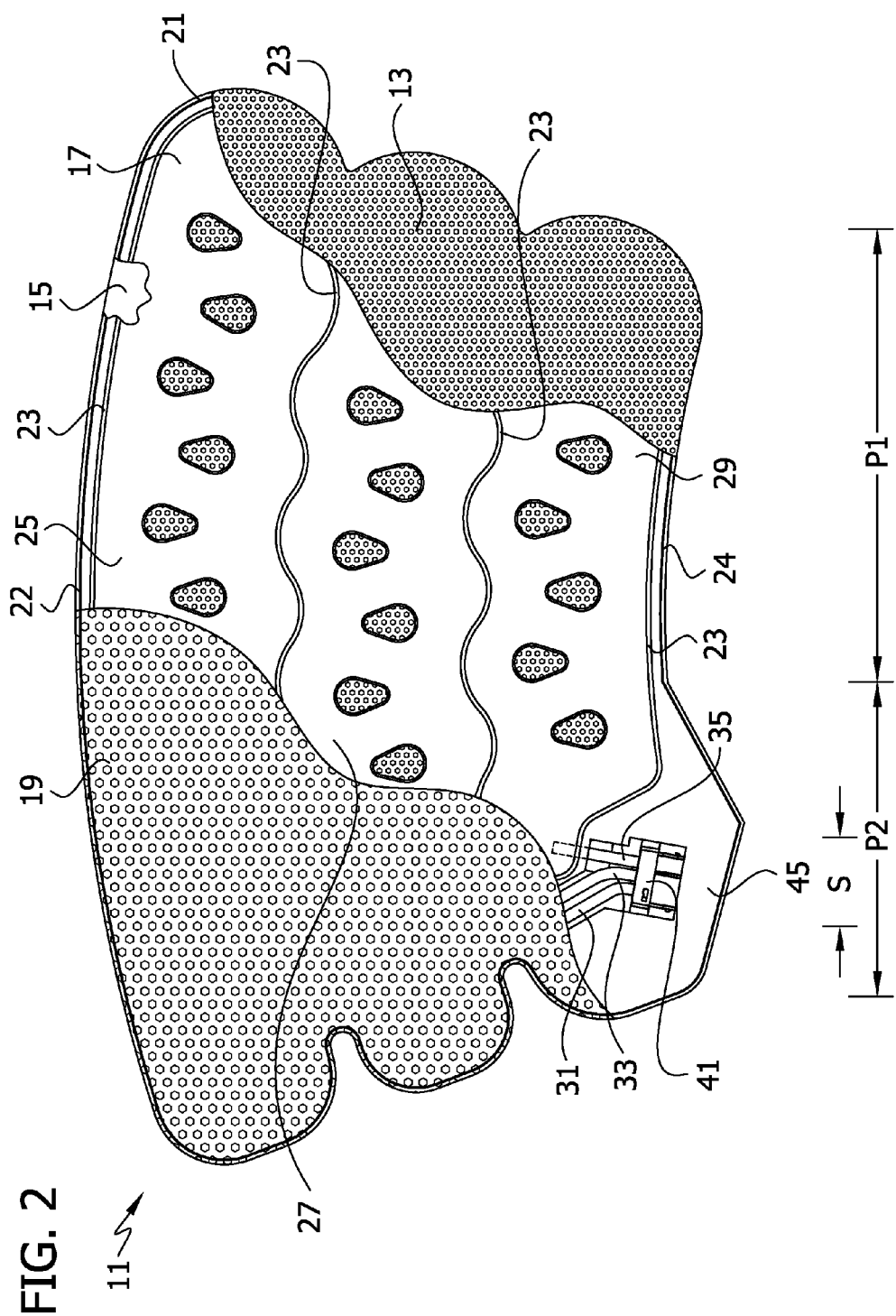

COMPRESSION GARMENT HAVING AN EXTENSION

FIELD OF THE INVENTION

The present invention generally relates to compression sleeves, and more particularly to a compression sleeve having an extension portion.

BACKGROUND OF THE INVENTION

Pneumatic compression sleeves can be used to apply intermittent compression therapy to a wearer's leg to prevent deep vein thrombosis (DVT). However, sleeves of this type can be used in other applications, including those in which a constant compression is applied during treatment. In a knee-length compression sleeve 1 of the prior art shown in FIG. 1, the sleeve comprises a plurality of inflatable bladders 3. Tubes 5 fluidly connect to respective bladders 3 to allow for independent inflation of each bladder. A connector 7 secured to distal ends of the tubes 5 is configured for attachment to a mateable connector (not shown) associated with additional tubing extending from a compression control unit (not shown) so that the control unit can selectively deliver pressurized air to the respective bladders 3.

The connector 7 is made of a hard plastic and can cause discomfort to the wearer when it comes into contact with the wearer's skin. Although the sleeve underlies the connector 7 and provides a barrier to contact with the skin, the sleeve and/or connector may move in use causing the connector to contact the skin past the distal or lower edge of the sleeve. Therefore, there exists a need for a compression sleeve that reduces the likelihood that the connector will come into contact with the wearer, thus reducing the discomfort caused by the sleeve.

SUMMARY OF THE INVENTION

In one aspect, a compression garment for applying compression therapy to a wearer's body generally comprises a compression sleeve having a proximal edge and a distal edge. The sleeve includes at least one bladder. A tube is attached to the bladder. A connector on the tube connects the tube to a source of compressed fluid for inflating the bladder. The distal edge of the compression sleeve has a first portion and a second portion jutting distally from the first portion. The second portion includes at least a section generally aligned with the connector and spaced distally of the connector Other objects and features will be in part apparent and in part pointed out hereinafter.

BRIEF DESCRIPTION OF THE DRAWINGS

FIG. 2 is a front view of a compression sleeve of the present invention having portions of the sleeve broken away.

Corresponding reference characters indicate corresponding parts throughout the drawings.

DESCRIPTION OF THE PREFERRED EMBODIMENTS

Figure 1:
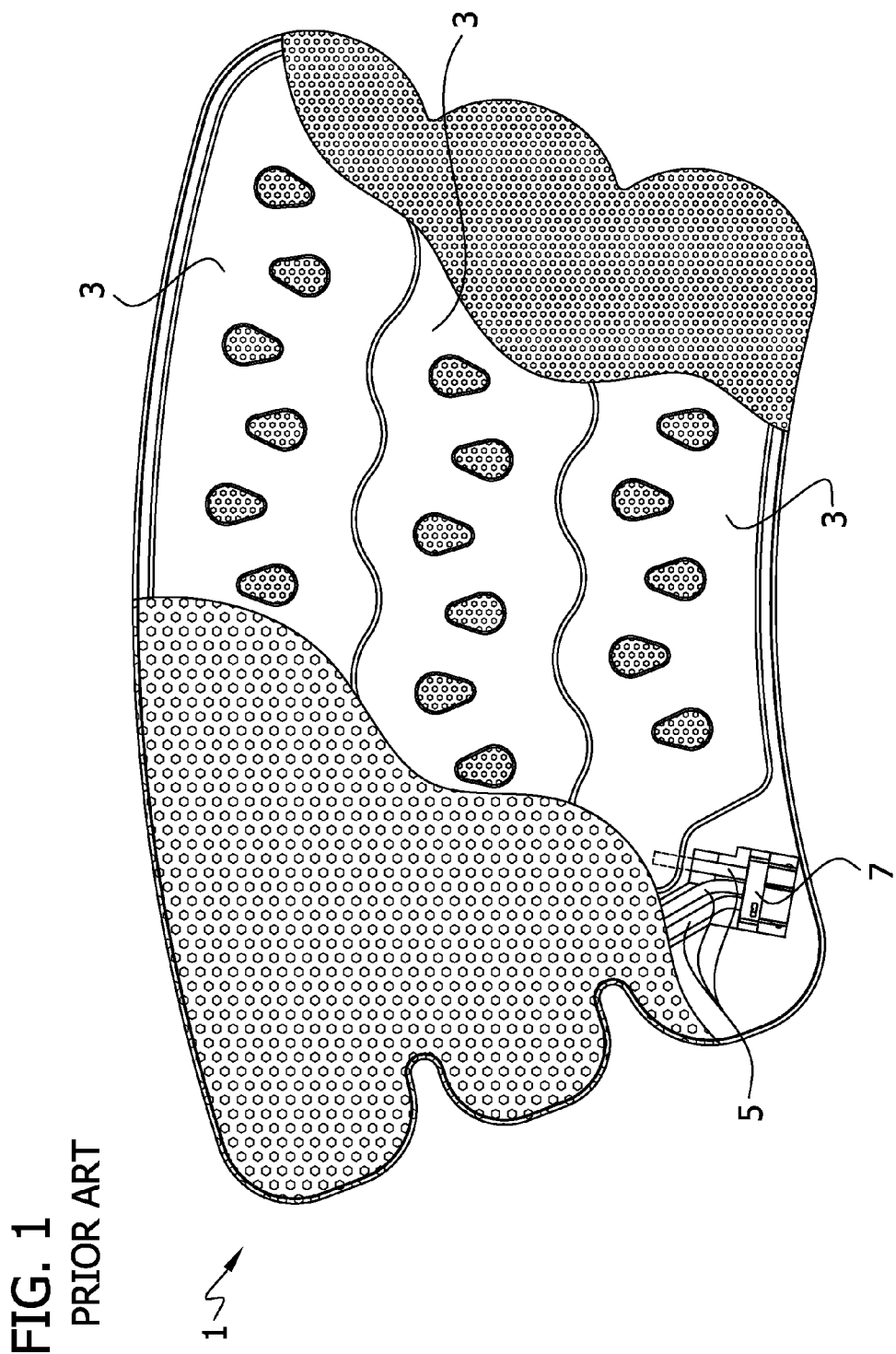
FIG. 1 is a front view of a compression sleeve of the prior art having portions of the sleeve broken away.

Referring now to FIG. 2, a compression garment (or "sleeve") of the present invention is generally indicated at 11. The compression garment is configured to apply repeated, sequential compression therapy to a limb of a wearer. The sleeve 11 is a knee-length sleeve sized and shaped for being disposed around a leg of the wearer. It will be understood that the compression sleeve may come in different configurations, such as a thigh-length sleeve. Other types of compression devices for being disposed about other limbs of the wearer's body are within the scope of this invention as well. These include devices that do not apply compression repeatedly and/or sequentially.

In the illustrated embodiment, the compression sleeve 11 comprises four layers secured together. The compression sleeve 11 comprises an inner layer, generally indicated at 13, on which a first intermediate layer (broadly, a first bladder layer), generally indicated at 15, is overlaid. A second intermediate layer (broadly, a second bladder layer), generally indicated at 17, overlies the first intermediate layer 15 and is secured thereto. An outer layer or cover generally indicated at 19, overlies and is secured to the second intermediate layer 17. The layers 13-19 may be secured together in any suitable manner as by radiofrequency welding, adhesive, or other chemical and/or mechanical process. In the illustrated embodiment, the layers 13-19 are secured about a periphery 21 of the sleeve 11 forming a proximal edge 22 and a distal edge 24. In use, the inner layer 13 is disposed most adjacent to the limb of the wearer and is in contact with the limb of the wearer, and the outer cover 19 is most distant from the limb of the wearer. The scope of the present invention is not limited to four layers. Also, it is understood that the configuration of the layers of the sleeve can be different than that disclosed in the illustrated embodiment.

The first and second intermediate layers 15, 17 respectively, each include a single sheet of elastic material (broadly, "bladder material"). For example, the sheets 15, 17 are made of a pliable PVC material. The inner and outer layers 13, 19 are made of a polyester material. The inner layer 13 can be absorbent and have a soft texture to provide a comfortable interface with the wearer's body. The second intermediate layer 17 is sealingly secured to the first intermediate layer 15 along bladder seam lines 23 defining a proximal bladder 25, an intermediate bladder 27 and a distal bladder 29, respectively, that are spaced apart longitudinally along the sleeve 11. It is understood that the intermediate layers 15, 17 may be secured together at other locations, such as around their peripheries. Also, the number of bladders may be other than three without departing from the scope of the present invention. As used herein, the terms "proximal", "distal", and "intermediate" represent relative locations of components, parts and the like of the compression sleeve when the sleeve is secured to the wearer's limb. As such, a "proximal" component or the like is disposed most adjacent to a point of attachment of the wearer's limb to the wearer's torso, a "distal" component is disposed most distant from the point of attachment, and an "intermediate" component is disposed generally anywhere between the proximal and distal components.

Each bladder 25, 27, 29 receives fluid from a source of compressed fluid (not shown) via a dedicated proximal bladder tube 31, intermediate bladder tube 33, or distal bladder tube 35, respectively for inflating the bladders. However, a tube line need not be dedicated to a bladder to practice the invention. Each tube 31, 33, 35 is disposed, at least partially, between the second intermediate layer 17 and the outer cover 19, and secured between the first and second intermediate layers 15, 17 to the respective bladders 25, 27, 29 by the respective bladder seam lines 23. Other ways of securing the tubes 31-35 to the bladders 25-29 are within the scope of the invention. Distal ends of the tubes 31, 33, 35 are ganged together using a connector 41 that is adapted to fluidly connect the tubes to the source of compressed fluid. The source of compressed fluid may be an air compressor under the control of a microprocessor that sequentially pressurizes the bladders as is generally known in the art. An exemplary air compressor is described in U.S. Pat. No. 5,876,359 to Bock, the disclosure of which is incorporated herein by reference.

The sleeve 11 includes a projecting tab or "shield" 45 including a second portion P2 of the distal edge 24 of the sleeve such that a section S of the second portion is disposed generally distal to the connector 41. In the illustrated embodiment, the shield 45 partially underlies the connector 41 and protects the wearer's skin from contact with the connector. It is understood that the shield 45 could completely underlie the connector 41 or alternatively, the connector could be disposed substantially proximal to the shield such that the shield does not underlie the connector. A first portion P1 of the distal edge 24 is disposed generally proximal to the section S and the connector 41. The second portion P2 juts distally from the first portion P1 such that the section S of the second portion is disposed generally distal to the first portion and the connector 41.

In the illustrated embodiment, the shield 45 comprises a V-shaped extension on the layers 13-19 of the sleeve 11. Configurations other than the V-shaped extension are within the scope of the invention. For instance, the extension can be rounded, square or any other suitable shape. It is understood that the shield 45 can be formed in just one of the inner and outer layers 13, 19 or in any one or combination of the layers 13-19 of the sleeve 11. The illustrated embodiment shows the shield 45 as an integral extension of the sheet material. However, it is within the scope of the invention for the shield 45 to be formed from a separate sheet material and permanently or releasably attached to the layers 13-19 in a suitable manner such as by hook and look fasteners. Additionally, the shield 45 can be formed from a material other than sheet material. The shield 45 increases the area of the sleeve 11 to provide a barrier for preventing the connector 41 from contacting the wearer's leg should the sleeve or connector move during use.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions without departing from the scope of the invention, it is intended that all matter contained in the above description and shown in the accompanying drawings shall be interpreted as illustrative and not in a limiting sense.

What is claimed is:

1. A compression garment for applying compression therapy to a wearer's leg, the garment comprising:
   a compression sleeve having a proximal edge and a distal edge, the sleeve including at least one bladder formed from at least one sheet of bladder material;
   a tube attached to the at least one bladder;
   a connector on the tube for connecting the tube to a source of compressed fluid for inflating the bladder to apply compression to the wearer's leg; and
   an outer layer over the sheet of bladder material;
   the distal edge of the compression sleeve having a first portion and a second portion jutting distally from the first portion forming a tab, the tab including at least a section generally aligned with the connector and spaced distally of the connector, the tab positioned with respect to the connector and projecting distally from a remainder of the distal edge of the compression sleeve a distance so that when the compression garment is secured to the wearer's leg the tab is interposed between the connector and a foot of the wearer to protect the wearer's foot from engagement by the connector.

2. The compression garment of claim 1 wherein the section of the second portion is disposed generally distal of the first portion of the distal edge of the compression sleeve.

3. The compression garment of claim 1 wherein the tab is V-shaped such that first and second edges of the tab converge at a single point defining a distal-most portion of the tab, distal edges of the tab being defined exclusively by the first and second edges.

4. The compression garment of claim 1 wherein the compression sleeve comprises a plurality of bladders and a tube attached to each of the bladders, each tube being connected to the connector.

5. The compression garment of claim 1 wherein the outer layer forms at least a part of the distally projecting tab.

6. The compression garment of claim 5 wherein the compression sleeve comprises an inner layer under the bladder.

7. The compression garment of claim 6 wherein the inner layer forms at least a part of the projecting tab.

8. The compression garment of claim 1 wherein the compression sleeve comprises an inner layer forming at least a part of the projecting tab.

9. The compression garment of claim 8 wherein the inner layer is absorbent and has a soft texture to provide a comfortable interface with the wearer's foot.

10. The compression garment of claim 1 wherein the connector and the tab are laterally offset from each other when the compression garment is opened and laid flat.

* * * * *